(12) United States Patent
Eberle et al.

(10) Patent No.: US 8,992,403 B2
(45) Date of Patent: Mar. 31, 2015

(54) CARTRIDGE AND CENTRIFUGE HAVING A CARTRIDGE

(75) Inventors: Klaus-Günter Eberle, Tuttlingen (DE); Roland Biset, Leuven (BE)

(73) Assignees: Terumo BCT, Inc., Lakewood, CO (US); Andreas Hettich GmbH & Co. KG, Tuttlingen (DE)

( * ) Notice: Subject to any disclaimer, the term of this patent is extended or adjusted under 35 U.S.C. 154(b) by 895 days.

(21) Appl. No.: 12/602,960

(22) PCT Filed: Jun. 4, 2008

(86) PCT No.: PCT/EP2008/056923
§ 371 (c)(1),
(2), (4) Date: Mar. 1, 2010

(87) PCT Pub. No.: WO2008/148808
PCT Pub. Date: Dec. 11, 2008

(65) Prior Publication Data
US 2010/0152013 A1    Jun. 17, 2010

(30) Foreign Application Priority Data
Jun. 5, 2007   (DE) .................. 10 2007 000 310

(51) Int. Cl.
 *B04B 7/08*   (2006.01)
 *B04B 5/04*   (2006.01)
(52) U.S. Cl.
 CPC ....... *B04B 5/0428* (2013.01); *B04B 2005/0435* (2013.01)
 USPC .............................................. 494/45; 210/782
(58) Field of Classification Search
 CPC ........ B04B 5/0428; B04B 7/16; B04B 15/00; B04B 2005/0407; B04B 2005/0435
 USPC .............................................. 494/45; 210/782
 See application file for complete search history.

(56) References Cited

U.S. PATENT DOCUMENTS 5,456,845 A * 10/1995 Nishimura et al. ............. 494/36
5,543,062 A    8/1996 Nishimura
(Continued)

FOREIGN PATENT DOCUMENTS

DE    196 22 050 A1   5/1996
DE    100 65 283 A1   12/2000
(Continued)

OTHER PUBLICATIONS

International Search Report dated Sep. 25, 2008 for PCT/EP2008/056926.
(Continued)

*Primary Examiner* — Timothy Cleveland
(74) *Attorney, Agent, or Firm* — John R. Merkling

(57) ABSTRACT

A cartridge (1) for accommodating blood bags (35) to be inserted into a centrifuge is used for the separation of blood components. Said cartridge (1) is provided with a partition wall (3) which separates a blood bag section (5) positioned radially inside from a product section (7) positioned radially outside, wherein a fixture (29) for a filter (31) is provided in the product section (7), a product transport path (36) which leads from the blood bag section (5) via the fixture (29) for the filter (31) to the product section (7). The product transport path (36) coming from the blood bag section (5) leads into the fixture (29) for the filter (31) radially from the outside and from below.

11 Claims, 11 Drawing Sheets

(56) References Cited

U.S. PATENT DOCUMENTS

Figure 1:
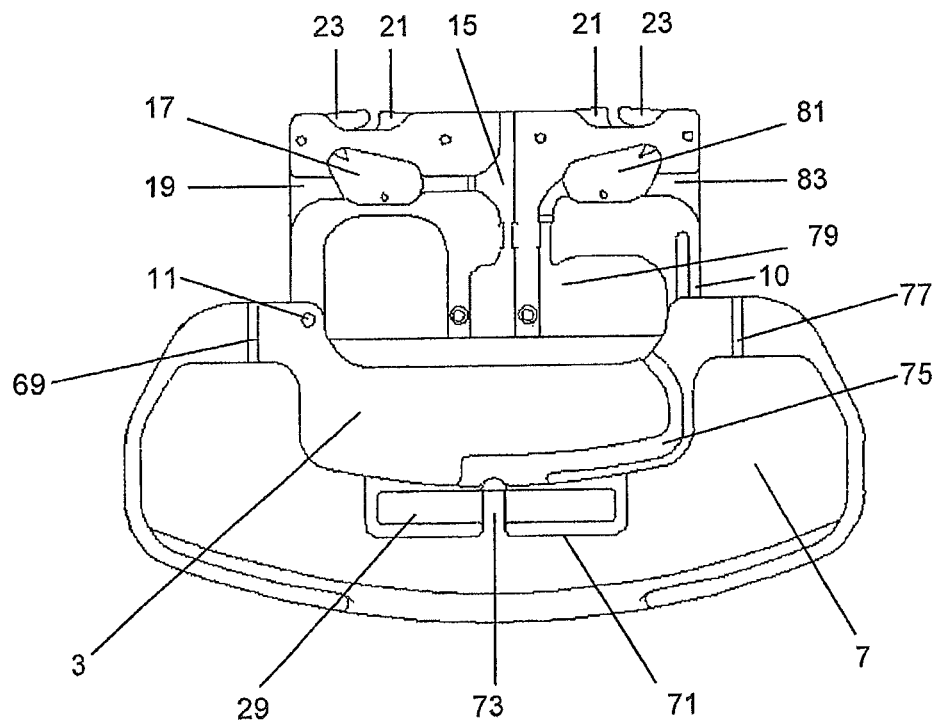

| | | |
|---|---|---|
| 5,734,464 A | 3/1998 | Gibbs |
| 5,795,317 A | 8/1998 | Brierton et al. |
| 6,234,989 B1 | 5/2001 | Brierton et al. |
| 6,361,518 B1 | 3/2002 | Brierton et al. |
| 7,166,217 B2 | 1/2007 | Holmes et al. |
| 7,194,087 B2 * | 3/2007 | Luginbill et al. ............. 379/455 |
| 7,981,019 B2 | 7/2011 | Holmes et al. |
| 2002/0085957 A1 | 7/2002 | Moore et al. |
| 2003/0176267 A1 | 9/2003 | Eberle |
| 2004/0026341 A1 * | 2/2004 | Hogberg et al. ............. 210/782 |
| 2008/0220959 A1 | 9/2008 | Holmes et al. |
| 2010/0170858 A1 | 7/2010 | Eberle et al. |
| 2011/0053201 A1 | 3/2011 | Eberle et al. |

FOREIGN PATENT DOCUMENTS

| | | |
|---|---|---|
| DE | 11 2004 000 569 T5 | 3/2006 |
| DE | 103 16 598 B4 | 5/2008 |
| DE | 102007000308 A1 | 12/2008 |
| DE | 102007000309 A1 | 12/2008 |
| DE | 102007000310 A1 | 12/2008 |
| EP | 0499891 A1 | 8/1992 |
| EP | 0616816 A2 | 9/1994 |
| EP | 1351772 B1 | 12/2001 |
| EP | 1512464 A2 | 3/2005 |
| EP | 1557187 A1 | 7/2005 |
| GB | 2174149 A | 10/1986 |
| WO | 02053292 A1 | 7/2002 |
| WO | 03089027 A2 | 10/2003 |
| WO | 2004069310 A2 | 8/2004 |
| WO | WO 2007024550 A2 * | 3/2007 |
| WO | 2010061863 A1 | 6/2010 |

OTHER PUBLICATIONS

International Search Report dated Sep. 25, 2008 for PCT/EP2008/056923.

International Search Report dated Oct. 14, 2008 for PCT/EP2008/056925.

International Search Report; International Application No. PCT/EP2011/050094; International Application Filing Date Jan. 5, 2011; Mail date May 2, 2011.

Written Opinion; International Application No. PCT/EP2011/050094; International Application Filing Date Jan. 5, 2011; Mail date May 2, 2011.

International Preliminary Report on Patentability; International Application No. PCT/EP2011/050094; International Application Filing Date Jan. 5, 2011; Date of completion of this report Apr. 4, 2012.

Millipore Corp.: MultiScreen Assay System, Centrifuge Alignment Frame, User Guide, May 2008.

Written Opinion for International Application No. PCT/EP2011/050093; Date of Mailing: May 10, 2011.

International Search Report for International Application No. PCT/EP2011/050093; Date of Mailing: May 10, 2011.

* cited by examiner

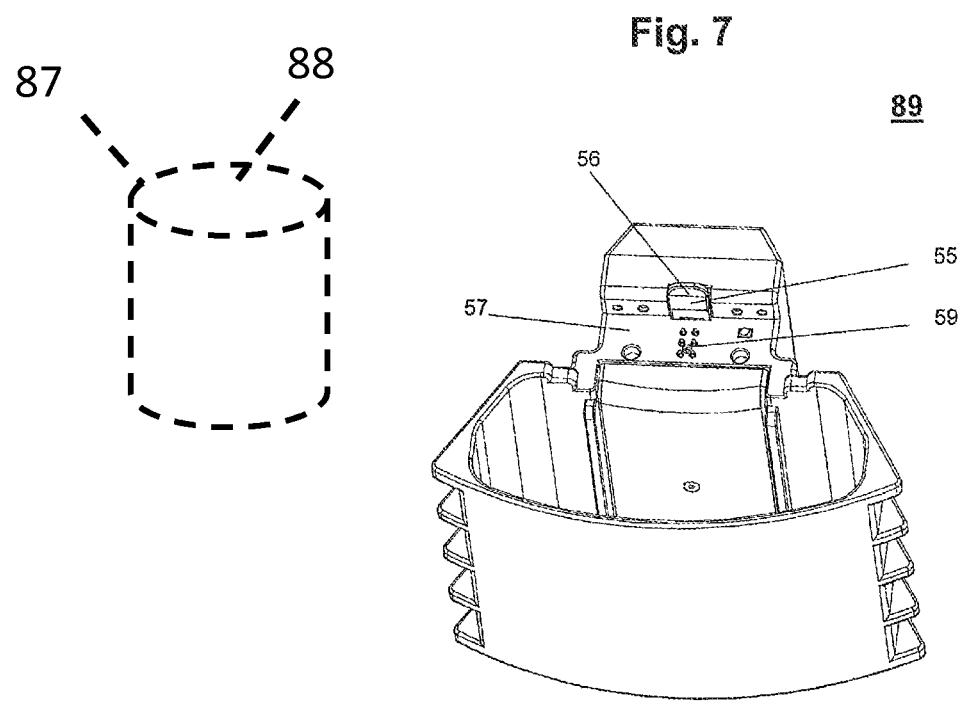

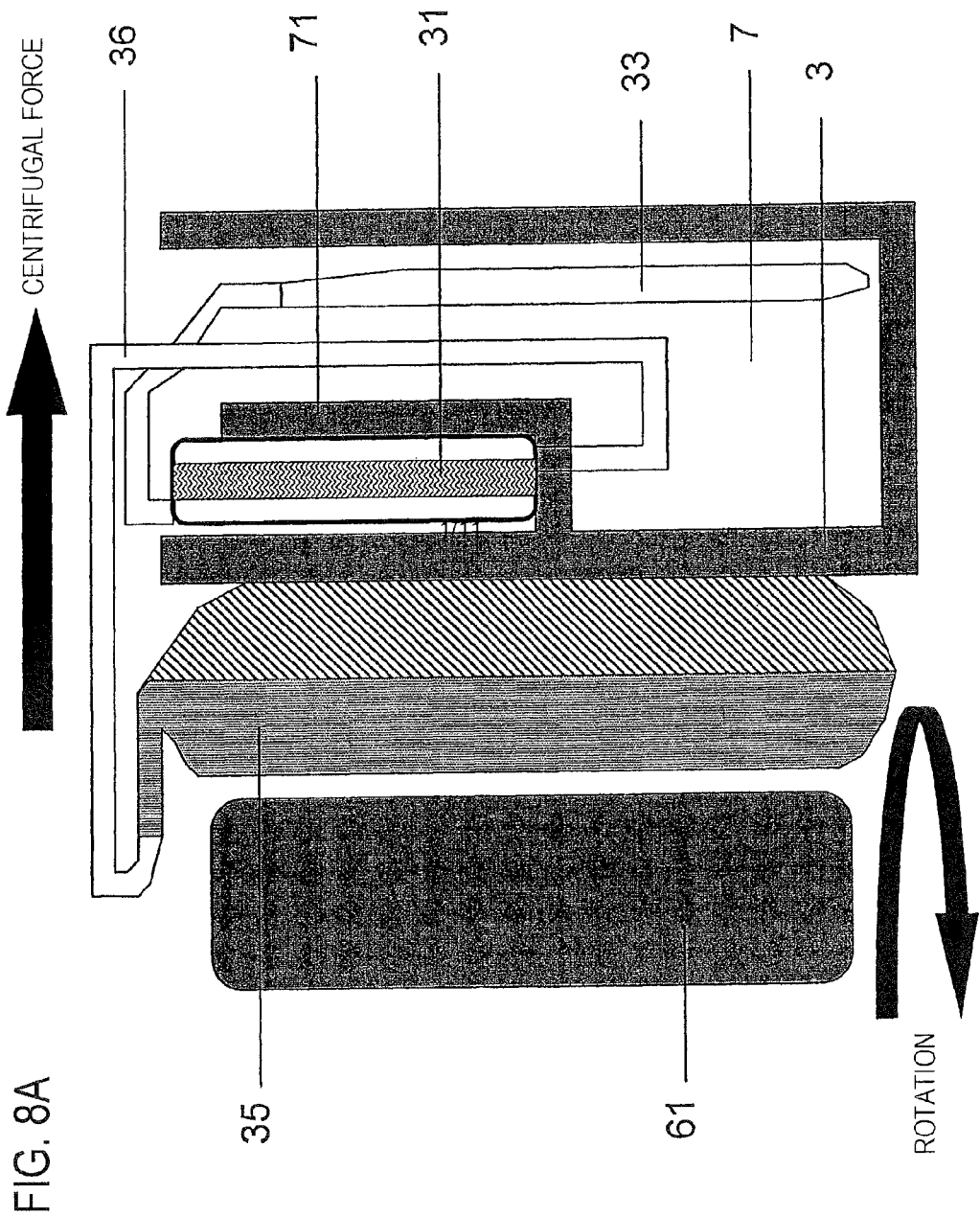

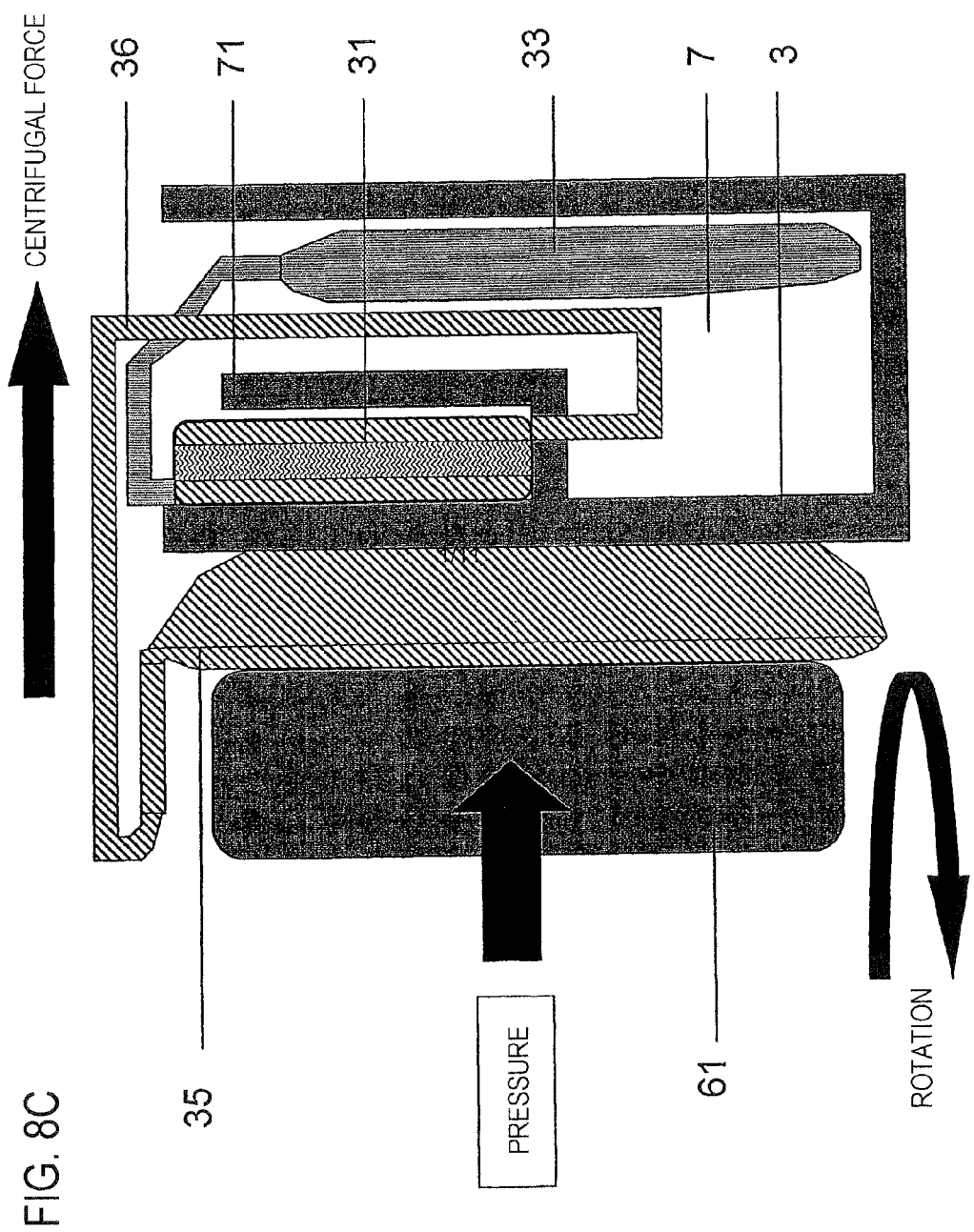

CARTRIDGE AND CENTRIFUGE HAVING A CARTRIDGE

CROSS REFERENCE TO RELATED APPLICATIONS

This application is a National Phase Application of Patent Application PCT/EP2008/056923 filed on Jun. 4, 2008, which claims priority to DE102007000310.4, filed Jun. 5, 2007, the contents each of which are incorporated herein by reference thereto.

TECHNICAL FIELD

The invention relates to a cartridge which is in particular provided for the application in a centrifuge in order to separate blood into its components, and to a centrifuge having such a cartridge.

STATE OF THE ART

In transfusion medicine the so-called blood component therapy has established itself since the beginning of the nineties. This means that, instead of a whole blood conserve, only those blood components are administered to the patient that the individual patient requires. By means of this separate administering of the individual blood components it is possible that one single blood conserve can provide optimal help to an average of 1.8 patients.

The essential blood components are
  the red blood cells in the so-called erythrocyte concentrate which are transfused in order to maintain the oxygen supply after severe loss of blood.
  the blood platelets in the thrombocyte concentrate which are administered in cases of coagulation disturbances (haemophilia), and
  the blood plasma which is administered in cases of coagulation disturbances and volume deficits. Apart therefrom, blood plasma is an essential basic component for the production of many medicaments.

The separation of the individual blood components which is defined as cell separation/isolation is known to be effected by treating the blood in a centrifuge. By means of centrifuging the individual blood components are separated and can then be filled separately into the respective containers for further use.

Such centrifuge is for example known from document EP 1 351 772 B1. According to this state of the art, a plurality of cartridges are arranged around a hub in a rotor of a centrifuge. The cartridges are firmly held in the rotor such that the blood bags are centrifuged in an upright position. Inside, the cartridges comprise accommodating devices for accommodating a blood bag containing whole blood and product bags in which the plasma and the erythrocyte concentrate are collected, respectively. In order to avoid a continued flowing and renewed mixing of the products after individual components have been separated, various clamping means are provided in the cartridge for clamping the individual tubes. Before removing the bags from the cartridge after separation has been effected the individual connecting tubes of the bags must be sealed by appropriate means. Only then can the clamps of the cartridge be opened, the bags be removed and the cartridge get prepared for accommodating a new set of bags.

After the separation and the drawing off of the plasma or the red blood cells, a mixture called "buffy coat" remains in the blood bags. This "buffy coat" consists mainly of platelets as well as white and red blood cells. For obtaining the platelets from this "buffy coat", the latter is diluted with an additive solution and this diluted "buffy coat" is then again separated into its components by centrifuging.

From document WO 03/089027 a system and a method for this purpose are already known. This document discloses a centrifuge in which a ring-shaped bag containing a mixture of "buffy coat" and additive solution is inserted into its single chamber. The blood components are then separated by means of a centrifuging operation and the separated components are transported via a tube line through a filter provided in the area of the hub to a collection container also provided in the area of the hub.

REPRESENTATION OF THE INVENTION

Technical Object

It is the object of the invention to provide an improved cartridge and a centrifuge including the cartridge that allow a better yield in cell separation/isolation and a more economic cell separation/isolation.

Technical Solution

The object of the invention is achieved by means of a cartridge according to claim 1 and a centrifuge according to claim 13. Advantageous embodiments of the invention are achieved according to the dependent claims.

A cartridge according to the invention for accommodating blood bags, which is provided for the application in a centrifuge for the separation of blood components, comprises a partition wall which separates a blood bag section positioned radially inside from a product section positioned radially outside. A fixture for a filter is provided in the product section. A product transport path leads from the blood bag section via the fixture for the filter to the product section. The product transport path is defined such that, coming from the blood bag section, it leads into the fixture for the filter radially from the outside and from below.

By means of the definition of the product transport path according to the invention and the positioning of the filter, it is ensured that red blood cells that are unintentionally transported through the tube collect at the outside and at the bottom surface of the filter due to the centrifugal force. Thus there is no risk that red blood cells are transported further into the product bag.

Advantageously, the fixture can comprise an outer wall which is positioned radially outside the partition wall and which is provided with a guiding means for guiding a tube led along the product transport path. Said guiding means can preferably be provided as a slot in the outside wall of the fixture.

Advantageously, the product transport path leads from the fixture for the filter via a recess formed above the partition wall on to the product bag section.

In particular, the blood bag section can comprise a cover and the product transport path can furthermore be defined by recesses in the cover, wherein the recesses are provided for holding the tube and/or a tube clamp.

The product transport path can lead from the fixture for the filter via second recesses formed in the cover to the product bag section. At least one photo sensor can be provided in one of the recesses and/or in one of the second recesses. Particularly, the second sensor allows an optimization of the yield in the cell separation/isolation.

After an "attention" signal output by the first sensor, the conveying speed of the product can be reduced in order to effect a precise measurement at the second sensor. Based on a predetermined composition of the product in the tube, a final signal for terminating the transportation together with a signal to close the tube clamps is output.

The second recesses can e.g. be formed in an essentially mirror-image manner relative to the first recesses.

In the cover of the cartridge, operating means for operating a tube clamp can be provided. The tube clamp is accommodated in one of the recesses or in one of the second recesses. In particular, also one tube clamp can be provided in one of the recesses and one tube clamp in one of the second recesses. The operating means for the tube clamps allow a purposeful and precise termination of the cell separation process while preventing undesired blood components from entering into the product bag.

The cover of the cartridge can be connected to the partition wall detachably at a first point, and pivotally at a second point. Then, when the cover is laterally pivoted out of the way, a blood bag section provided below the cover is freely accessible. This enables a fast changing of the blood bag in the blood bag section. The pivotal connection of the cover and the partition wall enables an easy positioning of the blood bag and one or more connecting tubes. Thus the tubes and the bag are optimally fixed within a short period of time.

The cartridge can furthermore be provided with a collecting tank which is positioned radially outside and which can embrace the product area and parts of the blood bag area. Advantageously, a handling device is provided inside the collecting tank in order to facilitate the handling of the collecting tank and of the cartridge partly embraced thereby. This handling device can e.g. be provided in the form of finger holes or handles.

The above-described cartridge is provided for use in a centrifuge for the separation of blood components. The centrifuge comprises a hub and a rotor which revolves around the hub. Advantageously, in the rotor, accommodating boxes are provided around the hub, which are also described as system boxes and which are used for accommodating the cartridges. However, it is also possible to use a centrifuge in which only one cartridge is accommodated. Each cartridge can be removed freely from the accommodating box and, thus, the centrifuge by activating a locking element connected to the accommodating box. These accommodating boxes can be detachably connected to the rotor.

This enables a fast exchanging of the cartridges containing the separated blood components by new cartridges containing blood components which are not yet separated while enabling a higher production yield in cell separation and an optimized equipment utilization.

In its non-operated state, the locking element can rest in a locking position. Thus, an immediate locking is achieved as soon as a cartridge is inserted into the accommodating box of the rotor. The locking element can furthermore be provided in the area of the hub or of the accommodating box.

Furthermore, the locking element can be provided at a support assigned to the cartridge. Accordingly, the cartridge is then accommodated between the support and one wall of the accommodating box and can only be moved upwards in one direction. This movement is, however, only possible by an operation of the locking element. This makes a secure positioning of the cartridge in the accommodating box possible for the centrifuging operation.

For holding the cartridge, the locking element in its non-operated state can be engaged with a side surface of the cover, located opposite the partition wall. A projection is formed on the locking element to prevent an upward movement of the cartridge.

The support can furthermore comprise a contact pad for establishing an electrically conductive connection between the accommodating box and the cartridge. The contact pad can consist of a plurality of electric contact points.

At the support, a pressing element can be provided so as to be radially movable into the area below the cover. This is used to press the separated components from the blood bag into the tube, through which they are further transported to the filter and into the product bag.

A first section of a line of the blood bag can advantageously lead upwards and radially inwards. This eliminates an undesired escape of liquids into the tube before the blood components are separated from each other.

The cartridge and the centrifuge according to the invention are, on the one hand, suited for the separation of cells and plasma from whole blood, but are also provided for extracting cells from the "buffy coat" that remains after a known centrifuging operation.

For this purpose, the "buffy coat" from several blood bags is collected together with an additive solution in a new blood bag, and is mixed. The new blood bag corresponds to the blood bag according to the invention. The new blood bag can advantageously be provided with a tube and/or a filter, particularly one provided for the filtering of leukocytes.

BRIEF DESCRIPTION OF THE ILLUSTRATIONS OF THE DRAWINGS

Figure 2:
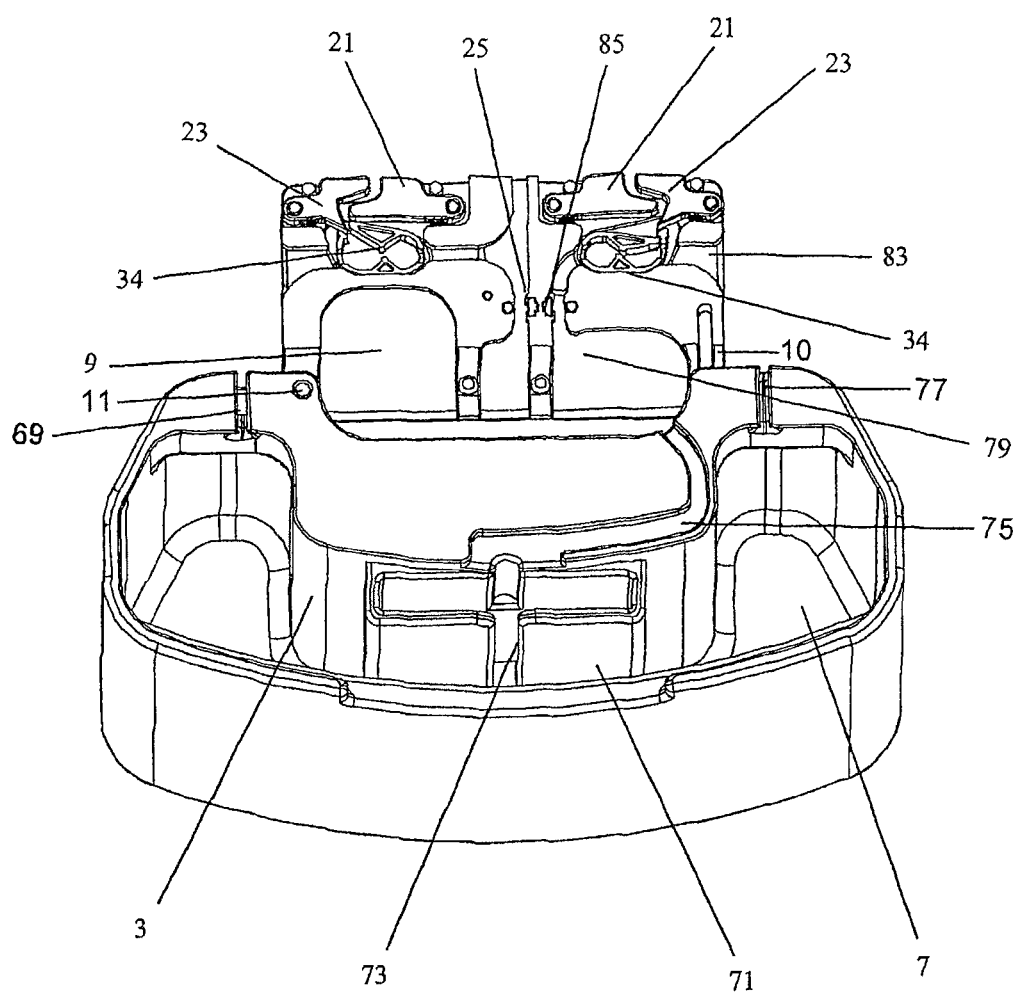
Figure 3:
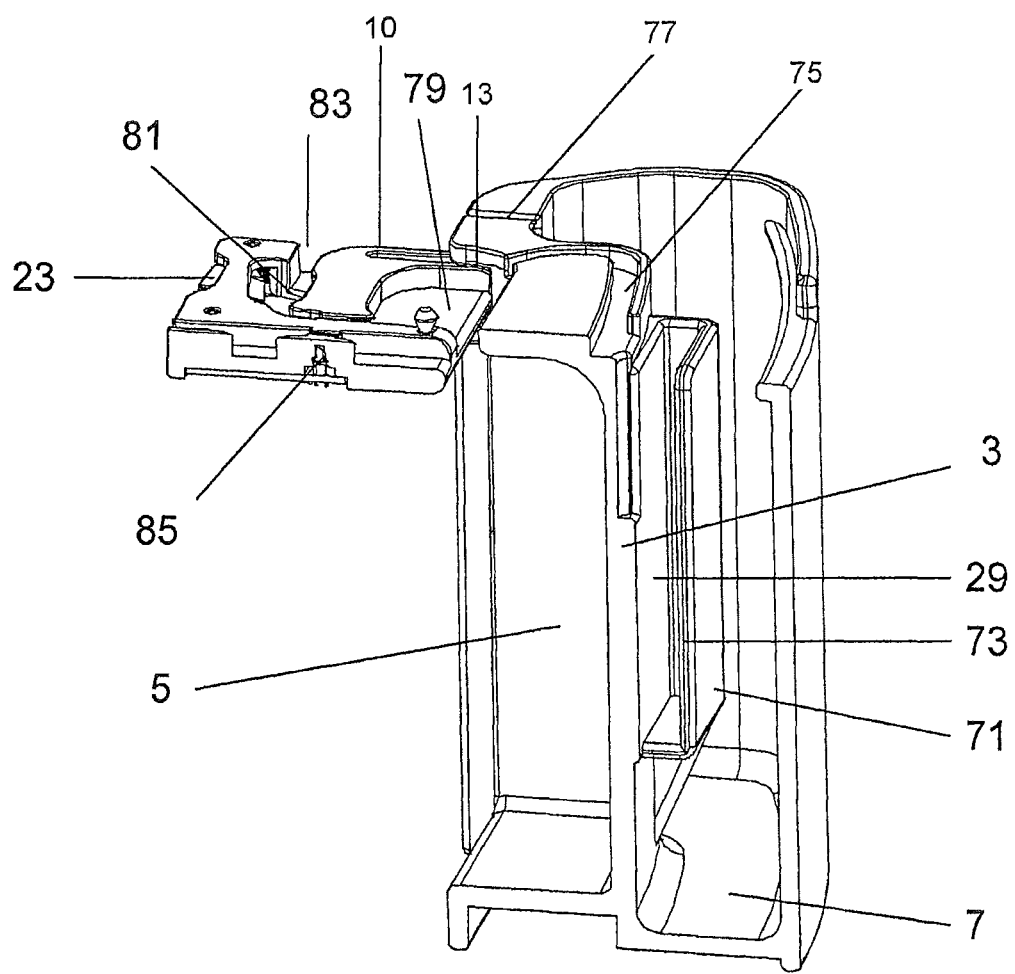
Figure 4:
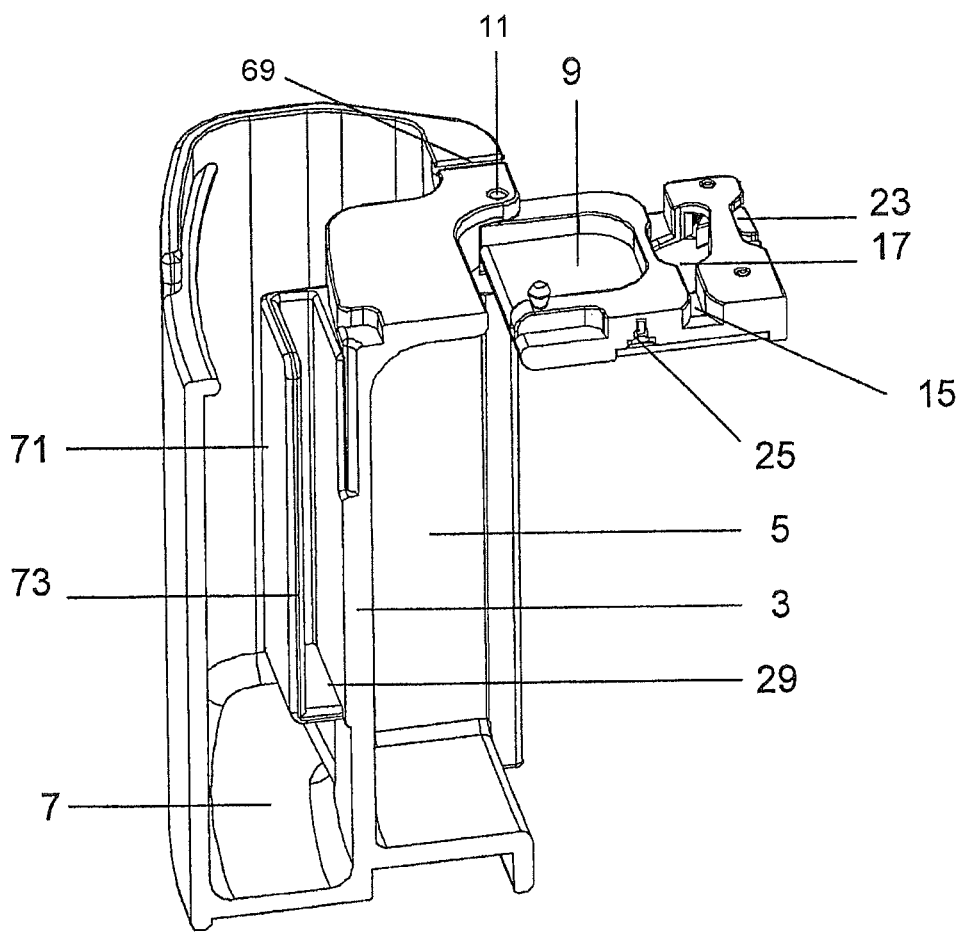
Figure 5:
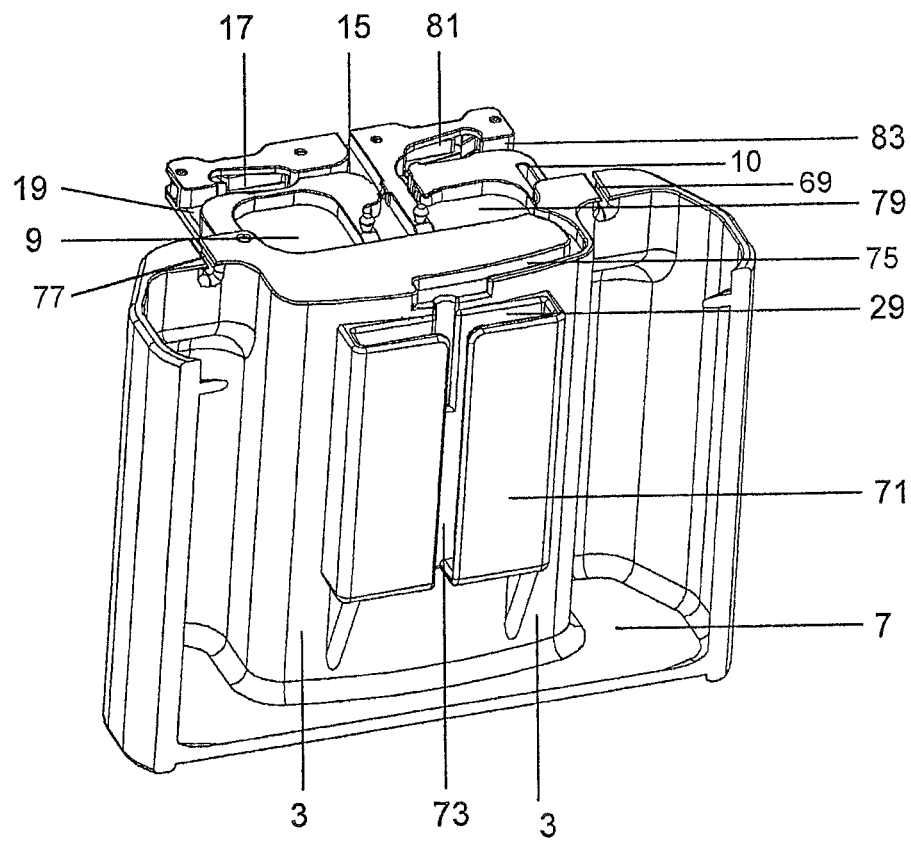
Figure 6:
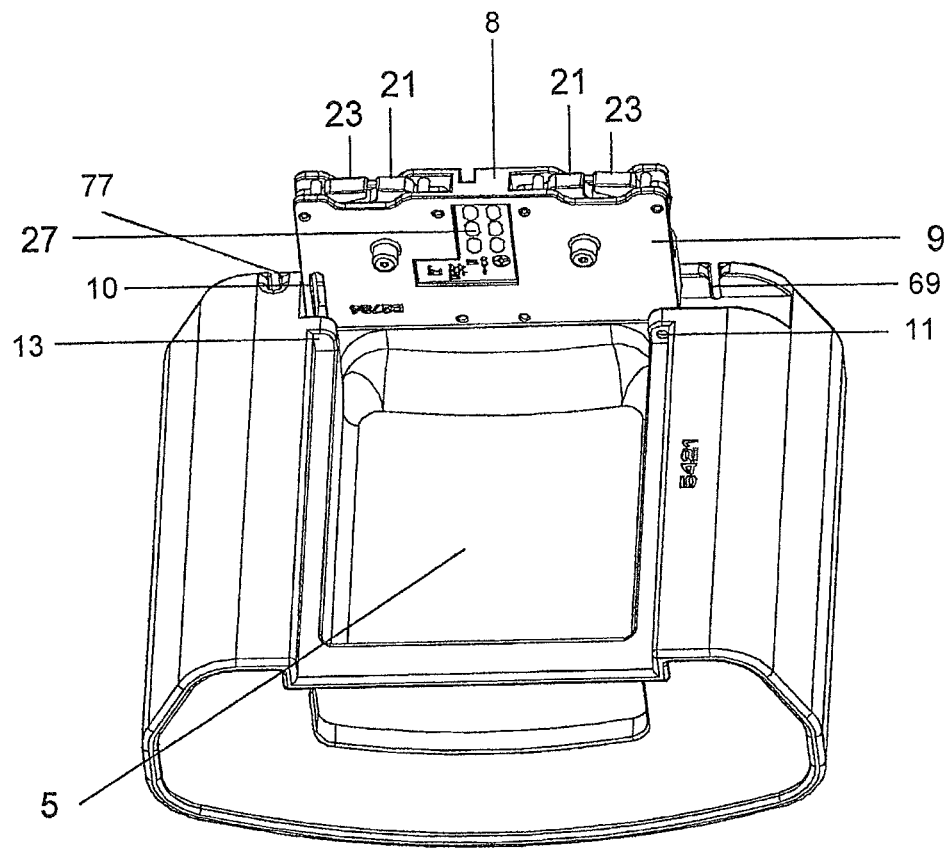
Figure 8B:
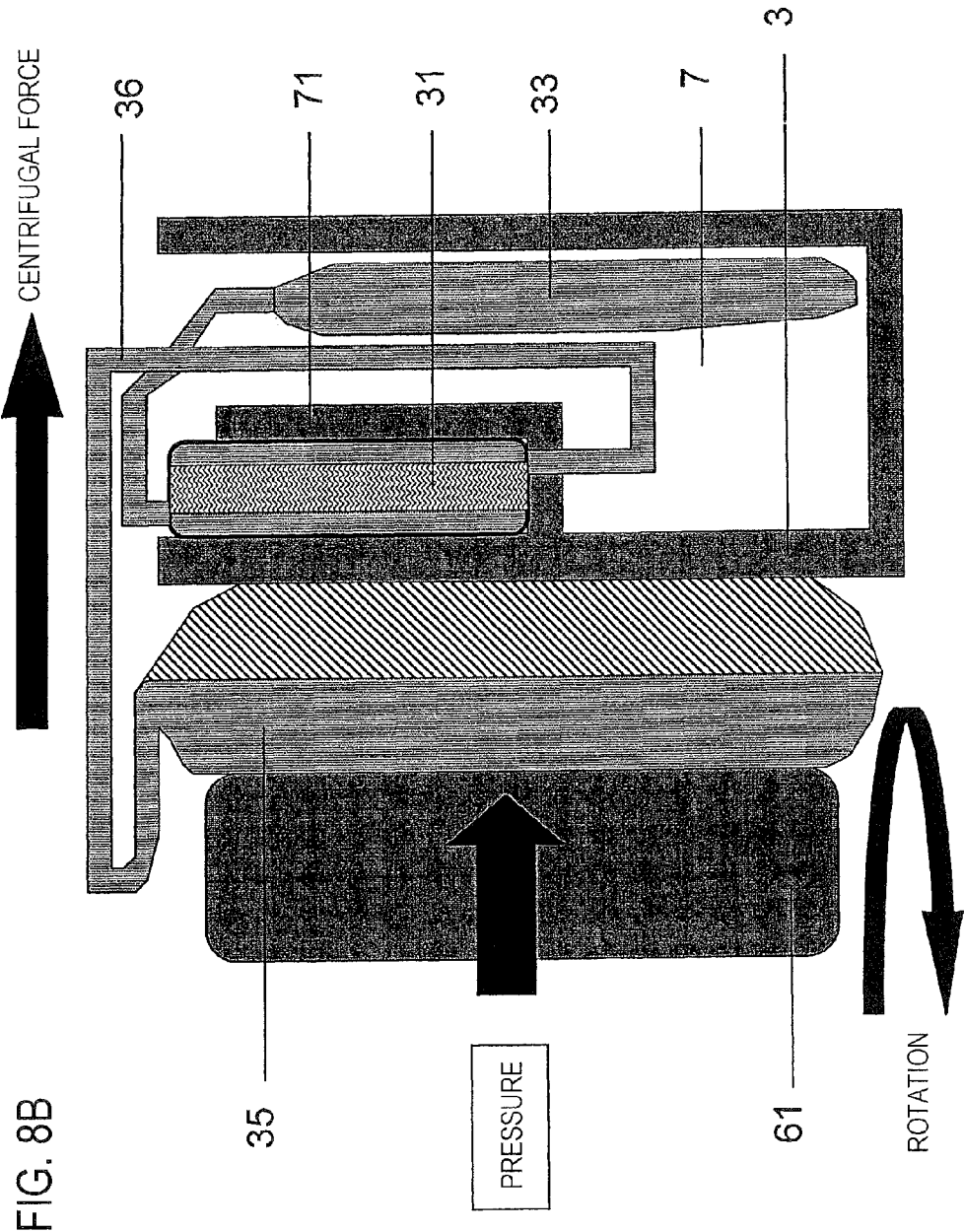
Figure 9:
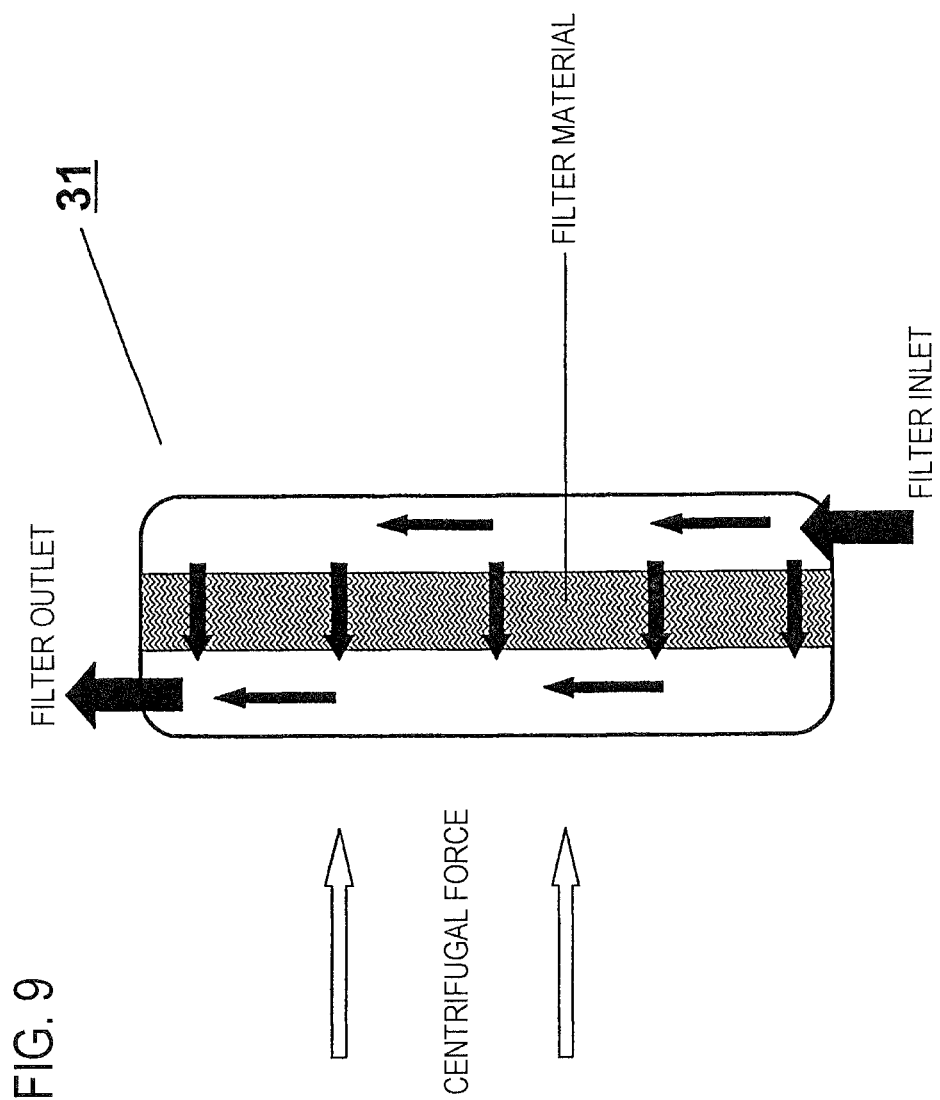

In the following, an embodiment of the invention is described by means of the Figures showing the following:

FIG. 1: a top view of the cartridge according to the invention,

FIG. 2: a perspective view of the cartridge,

FIG. 3: a perspective view of the cartridge, sectioned along a symmetry line,

FIG. 4: a sectional perspective view of the cartridge, supplementing the view of FIG. 4, FIG. 5: a further perspective and sectional view of the cartridge, FIG. 6: a bottom surface of a cover of the cartridge, FIG. 7: a perspective view of an accommodating box, and FIGS. 8a to 8c: schematic sectional views of the cartridge, from which the cell isolation can be seen, and FIG. 9 shows a flow of the blood product through the filter.

WAY(S) TO CARRY OUT THE INVENTION

An embodiment of the invention is described by means of FIGS. 1 to 9.

A cartridge 1 essentially consists of a partition wall 3 and a cover 9. The partition wall defines a blood bag section 5 and a product bag section 7. When the cartridge 1 is inserted into a system box 89 of the rotor of a centrifuge, the blood bag section 5 is located radially inside of the partition wall 3, whereas the product bag section 7 is located radially outside of the partition wall 3. An accommodating box 89 according to the invention is designated as system box 89.

A cover 9 is provided above the blood bag section 5. This has an essentially rectangular shape and, in its closed state, one of its longitudinal walls is in contact with the partition wall 3. At one corner point, the cover is pivotally mounted to the partition wall, whereas, at a second corner point, it is engaged with the partition wall 3 by means of a bolt 10. For opening the cover, pressure is applied onto the bolt 10 and then the cover is pivoted to the side. Thus, the blood bag section 5 is freely accessible and can be filled with a blood bag 35.

By means of the simple pivoting mechanism, a tube 36 and a blood bag 35 can quite easily be held in a desired position when the cover 9 is closed, and can be fixed in this predetermined position by the closing of the cover 9.

After the cover 9 has been closed, it is possible to insert the tube 36 into recesses 15, 19, which are formed in the top surface of the cover 9. A first photo sensor 25 is provided in the recess 15.

A tube clamp 34 in its closed state, which is delivered together with the blood bag and which is disposed on the tube, for example one produced by "Halkey Roberts", is accommodated in a recess 17 also formed in the top surface of the cover 9.

The end of the tube 36 which is the far end with respect to the blood bag 35 leads to the product bag section 7 and is there connected to a leukocyte filter 31 which is held in a fixture 29. The tube 36 is inserted into the leukocyte filter 31 radially from the outside and from below. The insertion of the filter 31 and the tube 36 is enabled by means of a slot 73 in an outside wall 71 of the fixture 29. Through the slot 73, the tube 36 connected to the filter 31 can be displaced from top to bottom, when the filter is inserted into the fixture, such that the tube leads to the filter radially from the outside and from below.

Behind the filter 31, the tube 36 leads, via second recesses 75, 79, 81, 83 which are provided in the cover 9 and which are positioned in an essentially mirror-image manner relative to the recesses 15, 17, 19, to the product bag 33, which is located radially outside of the fixture 29.

A second tube clamp 34 is provided in the recess 81. A second photo sensor 85 is located in the recess 79.

Inside the cover 9, two rods 21, 23 as operating means for operating the clamps 34 are respectively led through the cover such that one of their ends each slightly protrudes from a side surface 8 of the cover 9, which is located opposite the partition wall 3, and the other end is located in the area of the recess 17 accommodating the clamp 34. By applying a pressure onto one of the ends protruding from the side surface 8, the customary clamp 34 can thus be opened and closed. According to the embodiment, the tube clamps 34 can be operated individually as well as pneumatically.

After the cartridge 1 has been loaded, the cartridge 1 can be inserted into the system box 89 of the rotor of a centrifuge. When this is done, the side surface 8 of the cover 9, which is located opposite the partition wall 3, rests on a support 57 of the system box 89, which is provided in the area of a hub of the centrifuge. At the support 57, there is also a rod-shaped locking element 55 which has a projection 56 at its radial outside. By the insertion of the cartridge 1, the side surface 8 of the cover 9 slides over the projection 56 and moves the locking element 55 radially inward until the side surface 8 is positioned below the projection 56 and the locking element 55 springs back to its original position and thus prevents an upward movement of the cartridge 1. Now the cartridge 1 is firmly positioned between the outside wall of the system box 89 and the support.

According to the embodiment, the rotor of the centrifuge is designed for six system boxes 89 having one cartridge 1 each. After all cartridges 1 have been inserted, the centrifuge is started. By means of the centrifugal force the desired separation of the blood components is effected. Since the "buffy coat" diluted by an additive solution is in the blood bag 35, its lighter components will remain radially inside, whereas its heavier components, i.e. the red blood cells collect at the outside.

In order to transport the desired blood component—according to the embodiment, these are the platelets—in a high quality, i.e. without the admixture of other blood cells, from the blood bag, the separation of the components will be followed by a slight pressure being applied onto the blood bag by means of a known pressure pad 61, so that, after the clamps 34 have been opened, the solution rich in platelets begins to rise into the tube 36 leading upwards and radially inwards. The solution rich in platelets is led through the tube 36 into the leukocyte filter 31 into which it enters radially from the outside and from below.

In the leukocyte filter 31, the undesired leukocytes, i.e. the white blood cells, are removed. Due to the arrangement according to the invention of the tube 36 having the filter 31, the filtration is effected against the centrifugal force. Thus, heavier blood components, such as unintentionally transported red blood cells, are trapped in a front-end chamber of the filter, positioned radially outwards.

After having passed the leukocyte filter 31, the solution rich in platelets continues flowing through the tube 36 into a product bag 33, in which it is collected. Preferably the product bag 33 is already formed as the final storage bag for the product. The entire process is schematically illustrated in FIGS. 8a to 8c.

In order to remove any air that might be present in the filter, the flow speed is kept low for a certain volume quantity at the beginning of the product transfer, and thus it is enabled that the filter fills reliably and completely with the blood product. After the transfer of this predetermined volume quantity, the transport speed for a specified second volume quantity is increased by means of an appropriate control of the pressure pad. While this second volume is transported, there is hardly any risk that red blood cells contaminate the blood product (here: the thrombocyte concentrate). Should this nevertheless happen, this small number of red blood cells is collected in the lower and outer areas of the filter, due to the feeding of the tube from radially outside and below into the filter, and due to the effects of the centrifugal force.

After the second volume has been transferred, the first photo sensor is activated and the flow speed of the blood product in the tube 36 is reduced.

When the first photo sensor 25 detects a predetermined proportion of red blood cells in the thrombocyte-rich solution, it outputs a signal by means of which the flow speed is again reduced. Furthermore, the second photo sensor 85 arranged behind the filter 31 is activated.

During this phase, also a rather large number of red blood cells can enter into the filter 31 and even pass through it until the second photo sensor 85 detects a predetermined proportion of red blood cells in the blood product and outputs a signal for terminating the cell isolation process. By means of this signal, the tube clamps 34 are closed by activation of the rod 23, so that the red blood cells in the filter are reliably separated from the thrombocyte concentrate in the product bag. The operation of the rod is effected by means of an actuating mechanism provided in the system box 89.

As an alternative to the termination by means of the second photo sensor 85, the cell isolation process can also be terminated after a certain period of time has elapsed after the second photo sensor 85 has been activated.

In the embodiment, altogether six cartridges are provided in the centrifuge. The above described control of the cell isolation process in a cartridge 1 by means of a pressure pad 61, the opening and closing of the tube clamps 34, and the process control by means of the two photo sensors 25, 85 enables a continued cell isolation in the cartridges of the other system boxes 89, since the described process control operates individually for each combination of cartridge and system box.

For the transmission of the control and other electric signals, an electric contact pad in the form of individual contact points 59 is provided at the support 57 of the system box 89. At the bottom surface of the cover 9, contact surfaces 27 assigned to the contact points 59 are provided and get into contact with the contact points 59 when the cartridge 1 is inserted into the system box. For this purpose, the contact points 59 are spring-mounted.

For the purpose of an easier handling, on the one hand, and in case blood components should escape due to a damage of the bags 33, 35, the tube 36 or the filter 31, the cartridge 1 is inserted into a collecting tank 87 from a radially inward direction. In case of a damage, the escaping blood component is largely collected in the collecting tank so that there would only be little contamination of the system box 89 or of the rotor itself. In such a case, the system box 89 can be easily dismounted from the rotor.

After the cell isolation has been terminated, each of the cartridges 1 is removed by applying a slight pressure onto the locking element 55 in order to move this radially to the inside. Simultaneously, the cartridges 1 are seized at the finger holes 88 of the collecting tank 87 and lifted upwards out of the system box 89 of the centrifuge, and are immediately replaced by new, freshly loaded cartridges 1. During the subsequent cell isolation, the blood bags 35 and the product bags 33 can be removed from the exchanged cartridges 1 and these can be reloaded.

A cartridge (1) for accommodating blood bags (35) to be inserted into a centrifuge is used for the separation of blood components. The cartridge (1) has a partition wall (3) which separates a blood bag section (5) positioned radially inside from a product section (7) positioned radially outside, wherein a fixture (29) for a filter (31) is provided in the product section (7), a product transport path (36) which leads from the blood bag section (5) via the fixture (29) for the filter (31) to the product section (7). The product transport path (36) coming from the blood bag section (5) leads into the fixture (29) for the filter (31) radially from the outside and from below.

The invention claimed is:

1. A cartridge for accommodating blood bags, the cartridge being adapted to be inserted into a centrifuge radially outward from an axis of rotation of the centrifuge for the separation of blood components, the cartridge comprising:
    a blood bag section;
    a product section;
    a partition wall which separates the blood bag section from the product section, the blood bag section being positioned radially inside from the product section when the cartridge is inserted into the centrifuge;
    a fixture for a filter in the product section, the fixture being coupled to the partition wall and having an outside wall positioned radially outward from the partition wall when the cartridge is inserted into the centrifuge said fixture being configured to receive a filter such that an inlet to the filter is positioned at a bottom of said fixture and at said outside wall; and
    a product transport path which leads from the blood bag section via the fixture for the filter to the product section, the product transport path coming from the blood bag section along the outside wall of the fixture and into said bottom of the fixture, said outside wall having a guiding means for guiding a tube leading along the product transport path.

2. The cartridge according to claim 1, wherein the guiding means is a slot in the outside wall of the fixture.

3. The cartridge according to claim 1, wherein the product transport path to the product section leads from the fixture via a recess provided above the partition wall.

4. The cartridge according to claim 1, wherein the blood bag section comprises a cover, and the product transport path is furthermore defined by first recesses in the cover, wherein the first recesses are configured for holding a tube and a tube clamp.

5. The cartridge according to claim 4, wherein the product transport path leads from the fixture for the filter to the product bag section via second recesses provided in the cover.

6. The cartridge according to claim 5, wherein at least one photo sensor is provided in at least one of the first recesses and at least one of the second recesses.

7. The cartridge according to claim 5, wherein the second recesses are positioned in an essentially mirror-image relationship with respect to the first recesses.

8. The cartridge according to claim 6, further comprising: operating means for operating a tube clamp that is held in one of the first recesses and the second recesses.

9. The cartridge according to claim 8, wherein the cover is detachably connected to the partition wall at a first point, and the cover is pivotally connected to the partition wall at a second point, and the blood bag section provided below the cover is freely accessible when the cover is laterally pivoted away from the blood bag section.

10. The cartridge according to claim 1, wherein a collecting tank is positioned radially outside of the product section and wherein the collecting tank is positioned radially outside of the blood bag section when the cartridge is inserted into the centrifuge and the collecting tank surrounds portions of the blood bag section.

11. The cartridge according to claim 10, wherein the collecting tank further comprises a handling means for handling the tank and the cartridge.

\* \* \* \* \*